(12) United States Patent
Girard et al.

(10) Patent No.: US 9,241,961 B2
(45) Date of Patent: Jan. 26, 2016

(54) MEDICINAL PRODUCT FOR TREATING GASTROINTESTINAL ULCERS

(75) Inventors: Philippe Girard, Margny-les-Compiegne (FR); Marie-Emmanuelle Le Guern, Compiegne (FR); Marc Verleye, Remy (FR); Bernard Hublot, Compiegne (FR)

(73) Assignee: BIOCEDEX, Gentilly (FR)

( * ) Notice: Subject to any disclaimer, the term of this patent is extended or adjusted under 35 U.S.C. 154(b) by 291 days.

(21) Appl. No.: 12/962,031

(22) Filed: Dec. 7, 2010

(65) Prior Publication Data
US 2011/0135616 A1    Jun. 9, 2011

(30) Foreign Application Priority Data

Dec. 8, 2009   (FR) ..................................... 09 58734

(51) Int. Cl.
| | | |
|---|---|---|
| *A01N 63/00* | (2006.01) |
| *A61K 36/06* | (2006.01) |
| *C12N 1/16* | (2006.01) |
| *A61K 45/06* | (2006.01) |
| *A61K 31/192* | (2006.01) |

(52) U.S. Cl.
CPC ............... *A61K 36/06* (2013.01); *A61K 31/192* (2013.01); *A61K 45/06* (2013.01); *C12N 1/16* (2013.01)

(58) Field of Classification Search
None
See application file for complete search history.

(56) References Cited

U.S. PATENT DOCUMENTS

| | | |
|---|---|---|
| 6,649,383 B1 | 11/2003 | Cheung |
| 2006/0127489 A1 | 6/2006 | Crothers et al. |
| 2006/0140973 A1 | 6/2006 | Hublot et al. |
| 2007/0298013 A1 | 12/2007 | Altman |

OTHER PUBLICATIONS

Gotteland et al., Acta Paediatrica, 2005, vol. 94, p. 1747-1751.*
Konturek, P.C., J. Physiol. Pharmacol., 1997, vol. 48, No. 1, Abstract.*
Perenteryl, Merck Serono, downloaded from the website on 2013.*
Zanello et al., Curr Issues Mol. Biol., vol. 11, p. 47-58, published online on Jun. 25, 2008.*
Abraham et al., Digestive Diseases and Sciences, 2005, Vo. 50, No. 9, p. 1632-1640.*
Tanaka et al., The Journal of Pharmacology and Experimental Therapeutics, 2002, vol. 303, No. 3, p. 1248-1254.*
Girard et al., Nitric Oxide, 2005, vol. 13, p. 163-169.*
Preliminary French Research Report for FR 09 58610.
Gotteland M et al: "Systematic review : are probiotics useful in controlling gastric colonization by Helicobacter pylori?" Aliment. Pharmacol. Ther., vol. 23, (2006), pp. 1077-1086.

* cited by examiner

*Primary Examiner* — Kade Ariani
(74) *Attorney, Agent, or Firm* — B. Aaron Schulman, Esq.; Stites & Harbison, PLLC.

(57) ABSTRACT

The present invention relates to yeast cells for use in the prevention or treatment of gastric or intestinal ulcers.

6 Claims, 2 Drawing Sheets

MEDICINAL PRODUCT FOR TREATING GASTROINTESTINAL ULCERS

FIELD OF THE INVENTION

The present invention relates to a medicinal product for preventing or treating gastric or intestinal ulcers.

TECHNICAL BACKGROUND

Gastric or intestinal ulcers are manifested essentially by a loss of substance from a mucosal epithelial covering without any tendency for spontaneous healing and by lesion of the gastric or intestinal, notably duodenal, wall. It is generally considered that gastric or intestinal, notably duodenal, ulcers result from a mismatch between aggressive factors, such as acid and peptic gastric secretions, and defensive factors, such as prostaglandin synthesis, mucus and the surface epithelium.

Apart from *Helicobacter pylori*, gastrointestinal ulcers are mainly drug-induced. Thus, aspirin and the non-steroidal anti-inflammatories (NSAIDs), such as ibuprofen, notably inhibit the cyclooxygenases, leading to a decrease in prostaglandin synthesis and secretion of protective gastrointestinal mucus. In consequence, the gastrointestinal mucosa is exposed to acid attack by the gastric secretions.

NSAIDs with increased selectivity with respect to type 2 cyclooxygenase (COX-2), which is mainly inflammatory, relative to COX-1, forming the COXIB class of medicinal products, have been developed. However, the clinical studies conducted to date indicate that the COXIBs also present an increased risk of development of gastrointestinal ulcers (Yeomans (2002) *Journal of Gastroenterology and Hepatology* 17:488-494), which might reflect the role of COX-2 in the repair of mucosal lesions (Halter et al. (2001) Gut 49:443-453).

Thus, the problem of gastrointestinal ulcers linked to NSAIDs is particularly acute for persons treated long-term with these compounds, for example for controlling joint pain and inflammation.

At present, the main treatments used for gastrointestinal ulcers linked to NSAIDs employ two types of compounds (Yeomans (2002) *Journal of Gastroenterology and Hepatology* 17:488-494; Florent et al. (1990) *Acta Endoscopica* 20: 427-439):

(i) inhibitors of gastric secretions: proton pump inhibitors, such as omeprazole, or antagonists of the H2 histamine receptors, such as cimetidine and ranitidine;

(ii) stimulators of mucus secretion, such as the prostaglandins, and notably misoprostol (Graham et al. (1988) *Lancet* 2:1277-1280).

However, none of these treatments is completely satisfactory.

*Saccharomyces boulardii* (Ultra-Levure®) is a particular strain of the yeast *Saccharomyces cerevisiae*. This probiotic is mainly indicated as a supplement to rehydration for the treatment of diarrhoea. Its usefulness has notably been established in children (Villarruel et al. (2007) *Acta Paediatr* 96:538-541; Szajewska et al. (2007) *Aliment Pharmacol Ther* 25:257-264) and for diarrhoea associated with taking antibiotics (Surawicz et al. (1989) *Gastroenterology* 96:981-988; Kotowska et al. (2005) *Aliment Pharmacol Ther* 21:583-590) or with infections with *Clostridium difficile* (Surawicz et al. (2000) *Clin Infect Dis* 31:1012-1017).

SUMMARY OF THE INVENTION

The present invention follows from the unexpected demonstration, by the inventors, that *Saccharomyces boulardii* was able to reduce the number and area of gastric ulcers linked to ibuprofen in the rat.

Thus, the present invention relates to yeast cells for use in the prevention or treatment of gastric or intestinal ulcers.

The present invention also relates to the use of yeast cells for preparing a medicinal product intended for the prevention or treatment of gastric or intestinal ulcers.

The present invention also relates to a method of preventing or treating gastric or intestinal ulcers in an individual, in which a prophylactically or therapeutically effective amount of yeast cells is administered to the individual.

The present invention also relates to a pharmaceutical composition, or a composition intended for therapeutic use, comprising as active substances:

yeast cells, and at least one active principle having gastrotoxic activity, optionally together with a pharmaceutically acceptable vehicle.

The present invention also relates to a kit comprising:

in a first compartment, yeast cells;

in a second compartment, at least one active principle having gastrotoxic activity.

In a particular embodiment, the kit as defined above is used as a medicinal product or a product intended for therapeutic use.

Besides, in a particular embodiment of the above-defined yeast cells, use, method, pharmaceutical composition, composition intended for therapeutic use, or kit, no additional compound intended for treating gastric or intestinal ulcers, such as omeprazole for instance, is associated to the yeast cells of the invention.

DETAILED DESCRIPTION OF THE INVENTION

Figure 1:
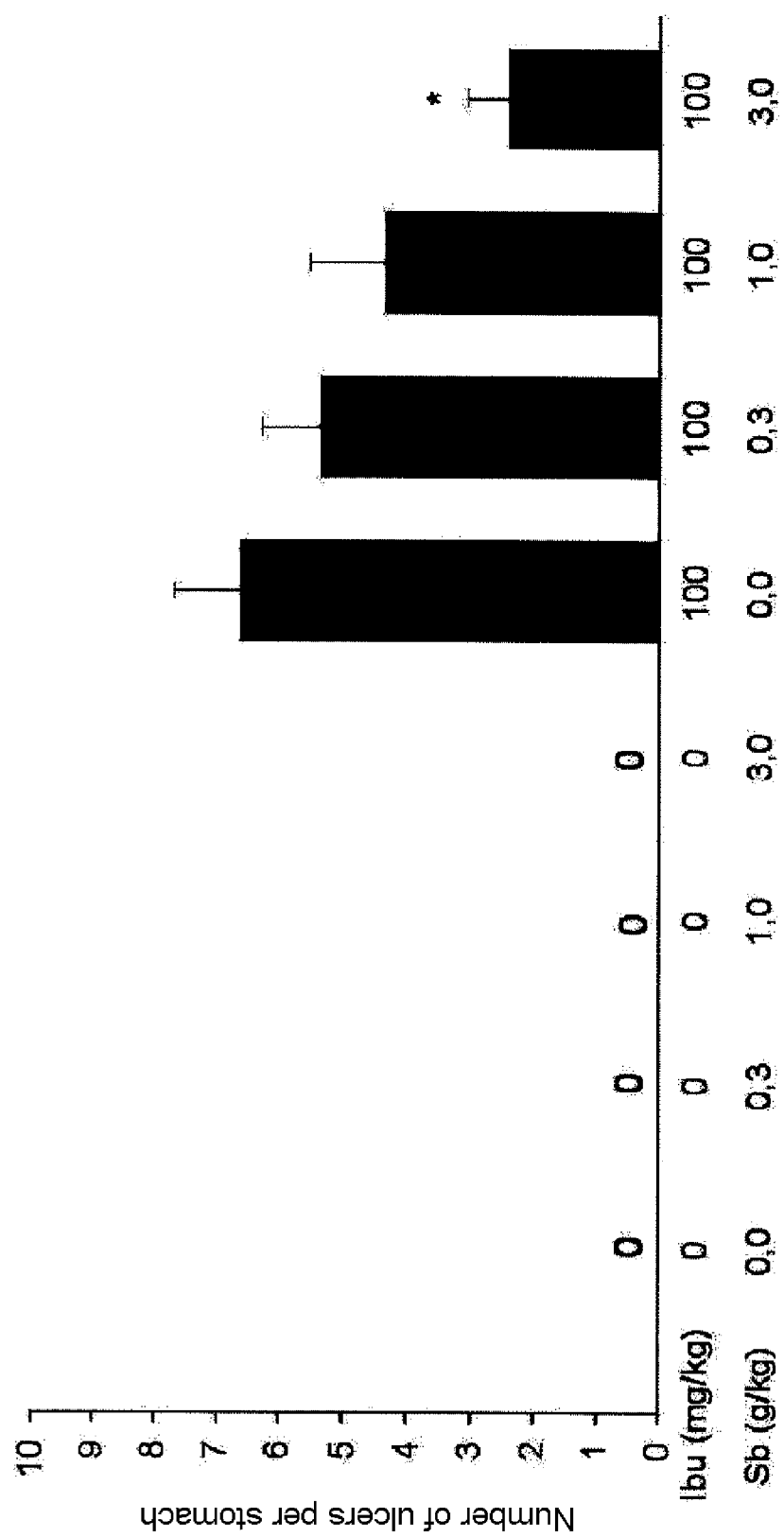
FIG. 1 shows the effect of *Saccharomyces boulardii* (Sb, oral) on the number of ulcers (ordinate) induced by repeated administration of ibuprofen (Ibu, oral) for 6 consecutive days. Sb is given for 6 days, 1 hour before the ibuprofen, and the number of ulcers is recorded on the sixth day.

The gastric or intestinal ulcers according to the invention, also called gastrointestinal ulcers, are preferably gastric or duodenal ulcers, also called peptic ulcers, and more preferably gastric ulcers. Even more preferably, the gastric or intestinal ulcers according to the invention are induced by an active principle having gastrotoxic activity.

As understood here, the expression "induced by an active principle" is synonymous with the expression "following administration of an active principle".

As understood here, the expression "active principle having gastrotoxic activity" encompasses all of the active principles of medicinal products that may cause gastric or intestinal ulcers according to the invention, notably as a side-effect. Of course, *Helicobacter pylori* is not an active principle having gastrotoxic activity according to the invention.

A person skilled in the art is perfectly aware of how to identify the medicinal products, and their associated active principles, that have gastrotoxic side-effects. In particular, an active principle having gastrotoxic activity according to the invention displays activity of inhibition of cyclooxygenase, notably of cyclooxygenase of type 1 (COX-1) and/or of type 2 (COX-2).

Thus, the active principle having gastrotoxic activity according to the invention is preferably a non-steroidal anti-inflammatory drug (NSAID) or aspirin. As an example of NSAID according to the invention we may notably mention ibuprofen. As understood herein, the term "aspirin" encompasses acetylsalicylic acid and all of its pharmaceutically acceptable salts, such as its lysine salts, and in particular DL-lysine acetylsalicylate.

Preferably, the active principle having gastrotoxic activity according to the invention is administered in the form of a capsule, a tablet or a sachet.

As understood here, the expression "yeast cells" includes viable or dead yeast cells, intact or in the form of debris. Preferably, at least a proportion of the yeast cells according to the invention are viable.

The viability of a yeast cell is defined as the capacity of a yeast cell to multiply. The number of viable cells in a sample can be estimated by determining the number of Colony Forming Units (CFU) contained in the sample.

As an example, the number of CFU of yeast cells in a liquid sample containing yeasts can be determined by spreading a specified volume of the sample on a solid medium, for example a gel medium, permitting growth of yeasts, and incubating the solid medium for a period of time, for example 48 h, and at a temperature, for example 30° C., permitting growth of yeast colonies. The number of colonies relative to the volume spread on the solid medium makes it possible to determine the number of CFU contained in the sample. A detailed protocol for determination of CFU according to the invention is notably described in Toothaker and Elmer (1984) *Antimicrobial Agents and Chemotherapy* 26:552-556 in the paragraph "*Assay for S. boulardii*". Moreover, when the yeast sample is in the form of a solid, for example a lyophilized powder, it is preferred to determine the number of CFU contained in the sample after solvating a specified mass of the sample in an aqueous solution, notably distilled water or a 0.9% NaCl solution at pH 7.

A "yeast" according to the invention is a fungus, preferably unicellular. Thus, the yeast cells according to the invention are preferably of the genus *Saccharomyces*, more preferably of the species *Saccharomyces cerevisiae* and even more preferably of the species *Saccharomyces boulardii*. *Saccharomyces boulardii* is well known to a person skilled in the art and is notably described in Hennequin et al. (2001) *J. Clin. Microbiol.* 39:551-559.

Particularly preferably, the cells of *Saccharomyces boulardii* according to the invention are obtained from medicinal products of the brand Ultra-Levure® or from deposits in the *American Type Culture Collection* (ATCC, USA) under reference 74012 or in the Collection Nationale de Culture et de Microorganismes (CNCM, France) under reference I-745.

Preferably, the yeast cells according to the invention are also lyophilized.

Advantageously, the viability and vitality of yeast cells obtained from lyophilizates are greater than can be obtained with other methods of preservation of yeast cells.

As understood here, "lyophilization" is a method of preservation in which the yeast cells are frozen and are then submitted to sublimation of the frozen water that they contain to give a lyophilizate in the form of dry yeast powder preferably containing less than 2% of water and more preferably less than 1% of water. Preferably, the lyophilized yeast cells are obtained from concentrates of yeast cells. Any type of method of lyophilization of yeast cells known by a person skilled in the art can be used. However, the yeast cells are preferably lyophilized according to the invention by means of the following method of lyophilization:

cultivate the yeast cells in a liquid nutrient medium until the cells reach a stationary phase;

concentrate the cultivated yeast cells and freeze the concentrate;

lyophilize the concentrate.

Preferably the yeast cells according to the invention are administered in the form of capsules or sachets.

Also preferably, the yeast cells according to the invention are administered at a dose of $0.5 \times 10^8$ to $100 \times 10^{10}$ CFU/kg/d or at a dose from 0.00125 g/kg/d to 25 g/kg/d.

As will be understood by a person skilled in the art, the amount of yeast cells to be administered per unit weight (kg) refers to the weight of the individual for whom the yeast cells are intended. Moreover, when the amount of yeast cells to be administered is expressed in unit of weight (g), the yeast cells are preferably in the form of a lyophilizate.

Preferably, the pharmaceutical composition as defined above and the kit as defined above are used for preventing or treating gastric or intestinal ulcers induced by the active principle that they contain.

Moreover, as will be evident to a person skilled in the art, when the kit according to the invention is used as a medicinal product, the yeast cells according to the invention and the active principle having gastrotoxic activity according to the invention can be administered together, or can be administered separately, i.e. according to different routes of administration and/or different regimens of administration.

As an example of a kit according to the invention, we may mention a box of medicinal product or a blister of medicinal product comprising, on the one hand, at least one composition comprising yeast cells according to the invention, for example a capsule or a sachet, and, on the other hand, at least one separate composition comprising an active principle having gastrotoxic activity according to the invention, for example a capsule, a tablet or a sachet.

EXAMPLE

The inventors determined the anti-ulcer effect of *Saccharomyces boulardii* in the model of gastric ibuprofen-induced ulcer in the rat according to the protocol of Abraham et al. (2005) *Dig Dis Sci* 50:1 632-1 640.

1. Material and Methods 1.1. Animals

Male Wistar rats obtained from Janvier weighing between 200 and 220 grams are used after acclimatization for at least 7 days in the animal house (temp.=22 ±2° C.; humidity: 50±20%; food SAFE "A04"; nyctohemeral cycle: 12 hours of light and 12 hours of darkness).

1.2. Protocol

On D1, the rat receives the test product or the solvent by the oral route. Then, 1 hour later, the rat receives ibuprofen at 100 mg/kg by the oral route, or the solvent for the control group. The rats receive these treatments for 6 consecutive days.

The animals go without food for 14-16 hours before the last administration of ibuprofen, but have access to drink. They are placed individually in a metal cage, the floor of which is a grating, to prevent coprophagia.

On D6 the rat is sacrificed. The stomach is then removed, and then opened along the great curve, rinsed with 0.9% NaCl, and placed in 10 ml of 2% formalin to fix the tissues.

Macroscopic evaluation of the gastric lesions is carried out as follows:

the stomach is spread out on a cork support with pins;
the number of ulcers on each stomach is counted;
the ulcerated area (mm$^2$) of haemorrhagic lesions is measured with a grid of squares (×10) and a stereo-microscope (Leica Wild M8) by measuring the length (mm) and width (mm) of each ulceration.

1.3. Products

*Saccharomyces boulardii* in lyophilized form (Ultra-Levure®, Biocodex, France, batch 3490) and ibuprofen (sodium salt, ref. 11892 Sigma) are dissolved in distilled water.

The batch of *Saccharomyces boulardii* used has a viability of $4.10^{10}$ CFU/g and an amount of 1 mg/ml of yeast corresponds to a concentration of $4.10^7$ CFU/ml. The values of colony forming units (CFU) reported are determined as indicated previously following the protocol of Toothaker & Elmer (1984) *Antimicrobial Agents and Chemotherapy* 26:552-556. The viability was determined by the plate counting technique.

The 10% formalin is diluted 5 times (15 ml bottle, ref. HT 50-1-1, Sigma).

1.4 Statistical Analysis

The statistical test used is an analysis of variance. When the result is non-random at the 5% threshold, a test is conducted for comparing the treated groups relative to the control group to determine the treated groups that differ significantly from the control group at the 5% threshold.

2. Results

Oral treatments with *Saccharomyces boulardii* at 0.3-1.0-3.0 g/kg/d and/or ibuprofen at 100 mg/kg/d do not alter the development of body weight of the rats relative to that of the untreated group.

Figure 2:
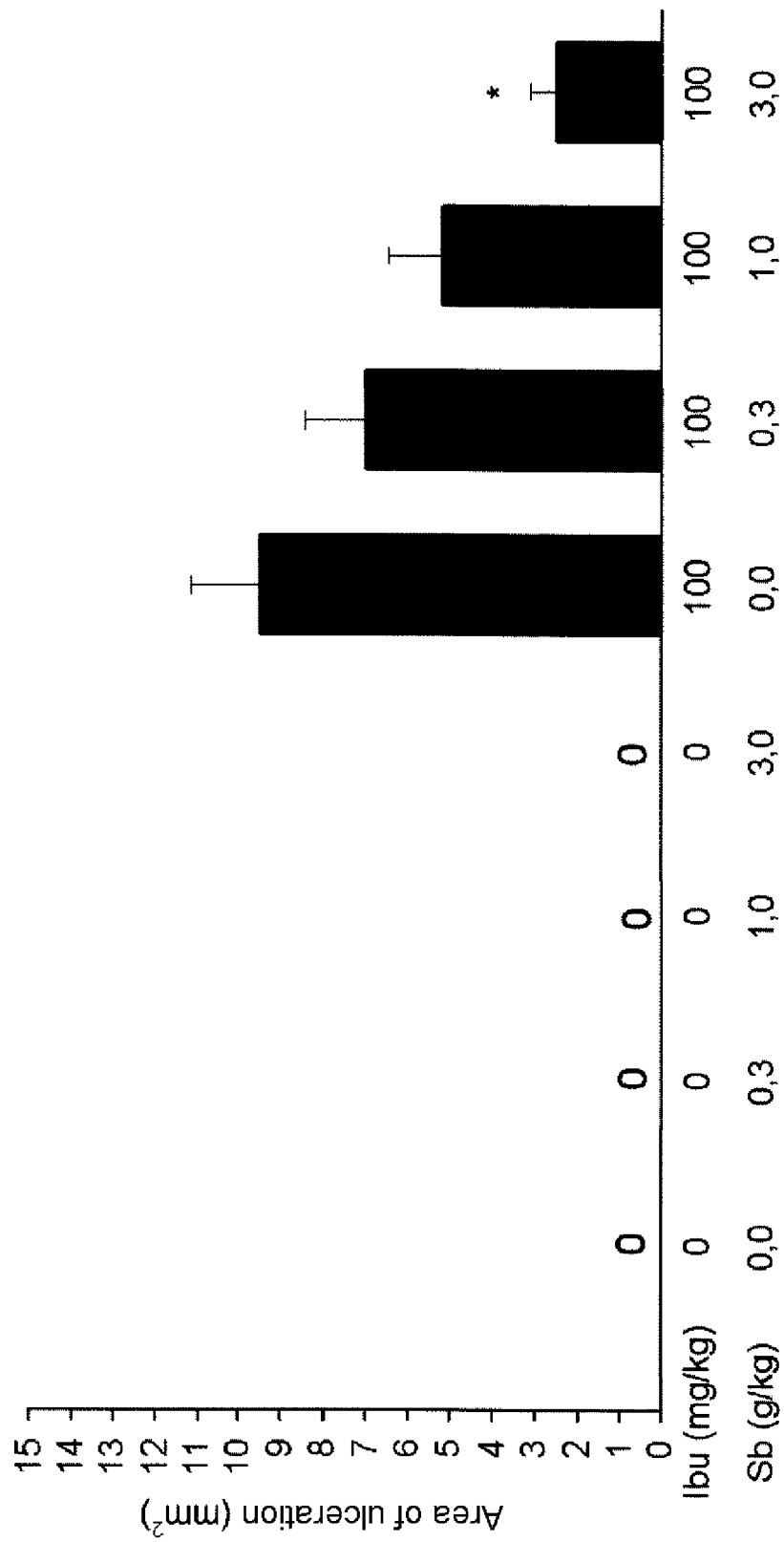
FIG. 2 shows the effect of *Saccharomyces boulardii* (Sb, oral) on the area of ulceration (ordinate, mm$^2$) induced by repeated administration of ibuprofen (Ibu, oral) for 6 consecutive days. Sb is given for 6 days, 1 hour before the ibuprofen, and the area of ulceration is measured on the sixth day.

In the control group and in those receiving only *Saccharomyces boulardii*, no ulcer is observed on the gastric mucosa (FIGS. 1 and 2).

In contrast, ibuprofen at 100 mg/kg/d for 6 days caused the appearance of 6.60±1.06 ulcers (FIG. 1) on the mucosa, with a total area of 9.40±1.72 mm$^2$ (FIG. 2).

The co-administration of *Saccharomyces boulardii* at 0.3-1.0-3.0 g/kg/d with ibuprofen shows a dose-dependent decrease in the ulcer count and the area of ulceration, with respectively 5.33±0.92; 4.32±1.21; 2.39±0.64 ulcers (FIG. 1), and 6.94±1.41; 5.10±1.30; 2.44±0.65 mm$^2$ (FIG. 2). At the highest dose, *Saccharomyces boulardii* leads to a significant decrease of 64% in the ulcer count and of 74% in the ulcerated area.

In conclusion, the co-administration of *Saccharomyces boulardii* and ibuprofen for 6 consecutive days shows that yeast possesses anti-ulcer properties in the model of ibuprofen-induced ulcer in the rat.

The invention claimed is:

1. A method of treating gastric or intestinal ulcers induced by a non-steroidal anti-inflammatory drug (NSAID) or aspirin in an individual, the method comprising co-administering the non-steroidal anti-inflammatory drug (NSAID) or aspirin and a prophylactic or therapeutic effective quantity of yeast cells of the species *Saccharomyces boulardii* to the individual.

2. The method of claim 1, wherein the NSAID is ibuprofen.

3. The method of claim 1, wherein the ulcers are induced by aspirin.

4. The method of claim 1, wherein the yeast cells are lyophilized.

5. The method of claim 1, wherein the yeast cells are administered in the form of capsules or sachets.

6. The method of claim 1, wherein the yeast cells are administered at a dose from $0.5 \times 10^8$ to $100 \times 10^{10}$ CFU/kg/d.

* * * * *